United States Patent
Cantrell et al.

(10) Patent No.: US 6,358,982 B1
(45) Date of Patent: Mar. 19, 2002

(54) HETEROCYCLYL SULPHONAMIDE DERIVATIVES

(75) Inventors: Buddy Eugene Cantrell, Fountaintown; Paul Leslie Ornstein, Carmel; Richard Lee Simon, Greenwood; Hamideh Zarrinmayeh, Carmel; Dennis Michael Zimmerman, Zionsville, all of IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/744,460

(22) PCT Filed: Jul. 28, 1999

(86) PCT No.: PCT/US99/17142

§ 371 Date: Jan. 23, 2001

§ 102(e) Date: Jan. 23, 2001

(87) PCT Pub. No.: WO00/06158

PCT Pub. Date: Feb. 10, 2000

Related U.S. Application Data

(60) Provisional application No. 60/094,978, filed on Jul. 31, 1998.

(51) Int. Cl.[7] ...................... A61K 31/445; C07D 211/06
(52) U.S. Cl. ...................... 514/331; 546/232; 546/227; 546/216; 548/566; 544/88; 544/162; 544/398; 514/327; 514/330
(58) Field of Search ................. 514/331, 330, 514/327; 546/232, 227, 216; 548/566; 544/88, 162, 398

(56) References Cited

U.S. PATENT DOCUMENTS

| 5,312,923 A | * 5/1994 | Chung et al. ............... 546/185 |
| 5,556,977 A | 9/1996 | Wayne et al. |
| 6,174,922 B1 | 1/2001 | Arnold et al. |

FOREIGN PATENT DOCUMENTS

| DK | 195 48 709 | 7/1997 |
| WO | WO 98/33496 | 2/1997 |
| WO | WO 00/66546 | 4/1999 |

OTHER PUBLICATIONS

U.S. application No. 09/744,413, Arnold et al., (WO00/06083).
U.S. application No. 09/744,457, Escribano et al., (WO00/06159).
U.S. application No. 09/744,414, Arnold et al., (WO00/06157).
U.S. application No. 09/744,418, Arnold et al., (WO00/06148).
U.S. application No. 09/744,419, Arnold et al., (WO00/06537).

* cited by examiner

*Primary Examiner*—Charanjit S. Aulakh
(74) *Attorney, Agent, or Firm*—Nelsen L. Lentz

(57) ABSTRACT

The present invention relates to the potentiation of glutamate receptor function using certain heterocyclyl sulphonamide derivatives. It also relates to novel heterocyclyl sulphonamide derivatives, to processes for their preparation and to pharmaceutical compositions containing them.

15 Claims, No Drawings

HETEROCYCLYL SULPHONAMIDE DERIVATIVES

This is a 371 of PCT/US99/17142 filed Jul. 28, 1999, now WO 00/06158 which claims priority to U.S. Provisional Application No. 60/094,978, filed Jul. 31, 1998.

The present invention relates to the potentiation of glutamate receptor function using certain heterocyclyl sulphonamide derivatives. It also relates to novel heterocyclyl sulphonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*,14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*,11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

It has now been found that cyclothiazide and certain heterocyclyl sulphonamide derivatives potentiate agonist-induced excitability of human GluR4B receptor expressed in HEK 293 cells. Since cyclothiazide is known to potentiate glutamate receptor function in vivo, it is believed that this finding portends that the sulphonamide derivatives will also potentiate glutamate receptor function in vivo, and hence that the compounds will exhibit ampakine-like behavior.

Accordingly, the present invention provides a compound of the formula:

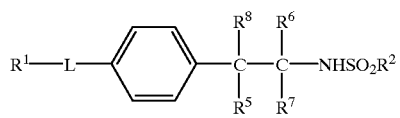

I wherein:
R$^1$ represents a carbon-linked 4 to 7 membered saturated heterocyclic ring containing as the hetero ring members a group NR$^a$ and a group X$^a$ in which X$^a$ represents CH$_2$, CO, O, S or NR$^b$; R$^a$ represents hydrogen or (1–4C)alkyl; and R$^b$ represents hydrogen or (1–4C) alkyl;

L represents a bond or a group of formula —(L$^a$)$_m$—X—(L$^b$)$_n$—in which X represents O, S, NR$^c$, CONH or NHCO; L$^a$ represents (1–4C)alkylene; L$^b$ represents (1–4C)alkylene; m is zero or 1; n is zero or 1; and R$^c$ is hydrogen or (1–4C)alkyl;

R$^2$ represents (1–6C)alkyl, (3–6C)cycloalkyl, (1–6C) fluoroalkyl, (1–6C)chloroalkyl, (2–6C)alkenyl, (1–4C) alkoxy(1–4C)alkyl, phenyl which is unsubstituted or substituted by halogen, (1–4C)alkyl or (1–4C)alkoxy, or a group of formula R$^3$R$^4$N in which R$^3$ and R$^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and either (a) one or two of R$^5$, R$^6$, R$^7$ and R$^8$ represents hydrogen; (1–6C)alkyl; aryl(1–6C)alkyl; (2–6C)

alkenyl; aryl(2–6C)alkenyl or aryl, or (b) two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof, provided that when L represents a group of formula —$(L^a)_m$—X—$(L^b)_n$ and m is 0, $R^1$ is not pyrrolidinyl.

According to another aspect, the present invention provides a method of potentiating glutamate receptor function in a mammal (including a human) requiring such treatment, which comprises administering an effective amount of a compound of formula I, or a pharmaceutically acceptable salt thereof as defined herein.

According to another aspect, the present invention provides the use of a compound of formula I, or a pharmaceutically acceptable salt thereof as defined herein for the manufacture of a medicament for potentiating glutamate receptor function.

According to yet another aspect, the present invention provides the use of a compound of formula I or a pharmaceutically acceptable salt thereof as defined herein for potentiating glutamate receptor function.

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated by the compounds of formula I and their pharmaceutically acceptable salts through their action as potentiators of glutamate receptor function. Such conditions include those associated with glutamate hypofunction, such as psychiatric and neurological disorders, for example cognitive disorders; neurodegenerative disorders such as Alzheimer's disease; age-related dementias; age-induced memory impairment; movement disorders such as tardive dyskinesia, Hungtington's chorea, myoclonus and Parkinson's disease; reversal of drug-induced states (such as cocaine, amphetamines, alcohol-induced states); depression; attention deficit disorder; attention deficit hyperactivity disorder; psychosis;

cognitive deficits associated with psychosis; and drug-induced psychosis. The compounds of formula I may also be useful for improving memory (both short term and long term) and learning ability. The present invention provides the use of compounds of formula I for the treatment of each of these conditions.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

Examples of values for a carbon-linked 4 to 7 membered saturated heterocyclic ring are azetidinyl, pyrrolidinyl, piperidinyl, morpholinyl, thiomorpholinyl, piperazinyl, hexahydropyrimidyl, tetrahydro-1,3-oxazinyl, tetrahydro-1,3-thiazinyl and hexahydroazepinyl.

Examples of more particular values for a carbon-linked 4 to 7 membered saturated heterocyclic ring are:

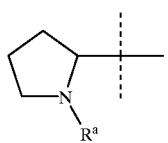

(a)

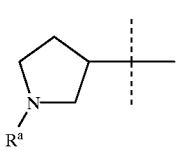

(b)

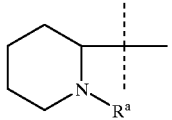

(c)

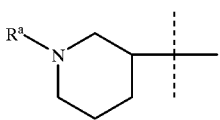

(d)

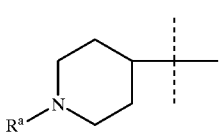

(e)

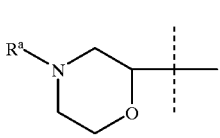

(f)

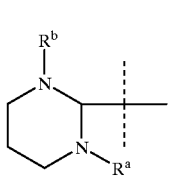

(g)

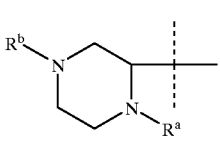

(h)

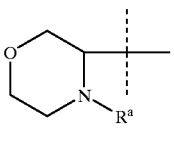

(i)

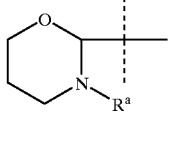

(j)

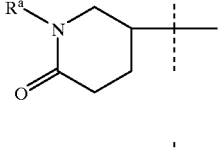

(k)

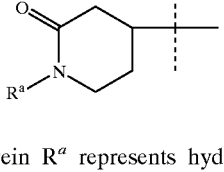

(l)

wherein $R^a$ represents hydrogen or (1–4C)alkyl; and $R^b$ represents hydrogen or (1–4C)alkyl Examples of values for $R^a$ are hydrogen and methyl.
Examples of values for $R^b$ are hydrogen and methyl.
Examples of values for $R^c$ are hydrogen and methyl.

Examples of values for $X^a$ are $CH_2$ and CO.

As used herein, the "aryl" as such or in the term "aryl (1–6C)alkyl" means phenyl or a polycyclic aromatic carbocyclic ring such as naphthyl.

The term (1–6C)alkyl includes (1–4C)alkyl. Examples of particular values are methyl, ethyl, propyl, isopropyl, butyl, isobutyl, t-butyl, pentyl and hexyl.

Examples of particular values for the term (2–6C)alkenyl are vinyl and prop-2-enyl.

The term (3–8C)cycloalkyl, as such or in the term (3–8C) cycloalkyloxy, includes monocyclic and polycyclic groups. Examples of particular values are cyclopropyl, cyclobutyl, cyclopentyl, cyclohexyl and bicyclo[2.2.2]octane.

The term halogen includes fluorine, chlorine, bromine and iodine.

Examples of particular values for the term fluoro(1–6C) alkyl are trifluoromethyl and 2,2,2-trifluoroethyl, and for chloro(1–6C)alkyl, chloromethyl.

Examples of particular values for the term (1–4C)alkoxy are methoxy and ethoxy.

An example of a particular value for the term (1–4C) alkoxy(1–4C)alkoxy is methoxymethyl.

Examples of particular values for the term (1–4C)alkylene are methylene, ethylene, propylene and butylene.

Examples of particular values for $R^1$ are 3-piperidinyl, 4-piperidinyl, 6-oxo-3-piperidinyl, 2-oxo-4-piperidinyl, N-methyl-3-piperidinyl and N-methyl-4-piperidinyl.

Examples of particular values for $L^a$ are methylene, ethylene, propylene and butylene.

Examples of particular values for $L^b$ are methylene, ethylene, propylene and butylene.

An example of a particular value for m is 1.

An example of a particular value for n is 0.

An example of a particular value for X is 0.

L preferably represents a bond or a group of formula $L^aX$.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, ethoxyethyl, phenyl, 4-fluorophenyl, or dimethylamino. Preferably $R^2$ is ethyl, 2-propyl or dimethylamino.

Preferably $R^3$ and $R^4$ each represent methyl.

Examples of a (1–6C)alkyl group represented by $R^5$, $R^6$, $R^7$ and $R^8$ are methyl, ethyl and propyl. An example of an aryl(1–C)alkyl group is benzyl. An example of a (2–6C) alkenyl group is prop-2-enyl. An example of a (3–8C) carbocyclic ring is a cyclopropyl ring.

Preferably $R^6$ and $R^7$ each represents hydrogen.

Preferably $R^5$ and $R^8$ each independently represents hydrogen or (1–4C)alkyl, or together with the carbon atom to which they are attached form a (3–8C) carbocyclic ring.

More preferably $R^8$ represents methyl or ethyl and $R^5$ represents hydrogen or methyl, or $R^5$ and $R^8$ together with the carbon atom to which they are attached form a cyclopropyl ring.

Especially preferred are compounds in which $R^8$ represents methyl and $R^5$, $R^6$ and $R^7$ represent hydrogen.

The compounds according to the invention may be prepared by:

(a) reacting a compound of formula

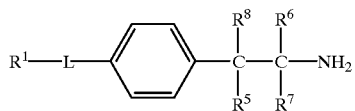

II with a compound of formula

III in which $Z^1$ represents a leaving atom or group;

(b) for a compound of formula I in which L represents a bond and $R^1$ represents a 6-oxo-3-piperidinyl group or a 2-oxo-4-piperidinyl group, rearranging a compound of formula

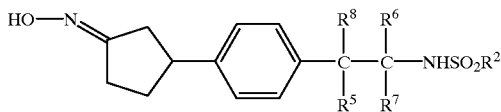

IV (c) for a compound of formula I in which L represents $-(L^a)_m-X-(L^b)_n-$ and X represents O, S or $NR^c$, reacting a compound of formula

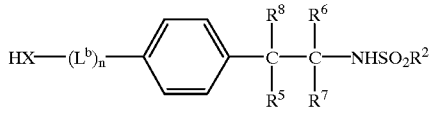

V with a compound of formula

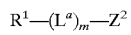

VI in which $Z^2$ represents a leaving atom or group, (d) for a compound of formula I in which L represents $-(L^a)_m-X-(L^b)_n-$ and X represents CONH or NHCO, reacting a compound of formula

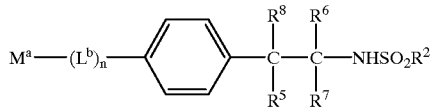

VII with a compound of formula

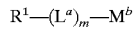

VIII in which one of $M^a$ and $M^b$ represents an amino group and the other represents a carboxyl group or a reactive derivative thereof; or (e) for a compound of formula I in which L represents a bond reacting a compound of formula

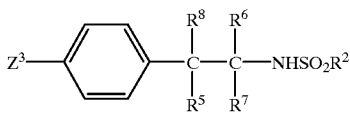

in which $Z^3$ represents a halogen atom, with a borane of formula

                                              X in which each of $R^x$ and $R^y$ represents a hydrocarbyl group, or together represents a hydrocarbyl group; followed, if desired, by forming a pharmaceutically acceptable salt thereof.

In step (a) of the process, the leaving atom or group represented by $Z^1$ may be, for example, a halogen atom such as a chlorine or bromine atom. The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene. Suitable solvents include halogenated hydrocarbons such as dichloromethane. The reaction is conveniently performed at a temperature in the range of from −20 to 100° C., preferably from −5 to 50° C.

Step (b) of the process represents an application of the well known Beckmann rearrangement. The rearrangement is conveniently performed in the presence of an organosulfonyl-oxyhalide, such as p-toluenesulfonyl chloride in the presence of a base, for example an alkali metal hydroxide such as sodium hydroxide. Convenient solvents include aqueous ethers, such as aqueous dioxane. The temperature is conveniently in the range of from −10 to 50° C. The 6-oxo-3-piperidinyl group or 2-oxo-4-piperidinyl group may then, if desired, be reduced to afford respectively a 3-piperidinyl or 4-piperidinyl group, for example using a borane, such as borane-tetrahydrofuran complex. Convenient solvents include ethers such as tetrahydrofuran. A 3-piperidinyl or 4-piperidinyl group may then, if desired, be alkylated, for example by reductive amination. For example, the group may be methylated using formic acid and formaldehyde.

In step (c) of the process, the leaving atom or group represented by $Z^2$ may be, for example, a halogen atom such as a chlorine or bromine atom. The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene. Suitable solvents include halogenated hydrocarbons such as dichloromethane. The reaction is conveniently performed at a temperature in the range of from −20 to 100° C., preferably from −5 to 50° C.

Step (d) of the process corresponds with the well known acylation of an amine. Examples of a reactive derivative of a carboxyl group thus include acyl halides, such as the chloride, and anhydrides.

The halogen atom represented by $Z^3$ in step (e) of the process may be, for example, a bromine atom. In the borane, the groups $R^x$ and $R^y$ may together represent, for example, cyclo-1,5-octyl. The reaction is conveniently performed in the presence of a tetrakis (triarylphosphine)palladium(0) catalyst, such as tetrakis (triphenylphosphine)palladium(0), and a base, such as potassium carbonate or potassium phosphate. Convenient solvents for the reaction include aromatic hydrocarbons, such as toluene. The temperature is conveniently in the range of from 0 to 150° C., preferably from 75 to 120° C. The borane starting material may be prepared by reacting a corresponding carbon-linked 4 to 7 membered monounsaturated heterocyclic compound, such as 2,5-dihydropyrrole, with an appropriate organoborane, such as 9-borabicyclo[3.3.1]nonane (9-BBN).

The compounds of formula II are known or may be prepared by conventional methods, for example by reducing a corresponding amide or nitrile using borane.

The compounds of formula IV may be prepared by reacting a compound of formula

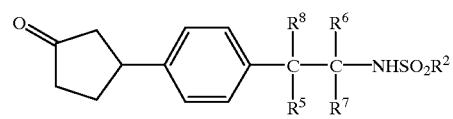                                              XI with hydroxylamine or an acid addition salt thereof.

The compounds of formula XI may be prepared by reducing a compound of formula

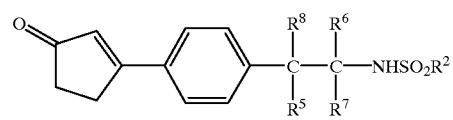                                              XII for example by catalytic hydrogenation in the presence of a Group VIII metal catalyst, such as palladium on carbon.

The compounds of formula XII may be prepared by reacting a compound of formula IX with 3-tributyltin-2-cyclopenten-1-one in the presence of dichlorobis(triphenylphosphine)palladium(II). Convenient solvents include ethers such as tetrahydrofuran. The temperature is conveniently in the range of from 0 to 100° C. The tributyltin compound may be prepared by reacting hexabutylditin with butyl lithium, followed by 3-ethoxy-2-cyclopenten-1-one at a reduced temperature.

The compounds of formula IX may be prepared by reacting a compound of formula XIII

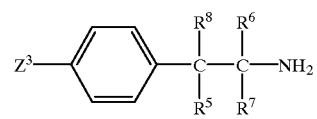                                              XIII with a compound of formula III according to the method of process (a) above.

The compounds of formula V may be prepared by reacting a compound of formula

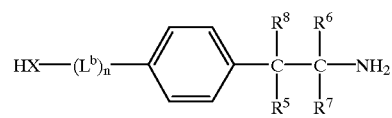                                              XIV or a derivative thereof substituted on X with a protecting group, for example a benzyl group, with a compound of formula III, according to the method of step (a) above. A benzyl protecting group may be removed, for example, by reaction with ammonium formate in the presence of palladium on carbon. A t-butoxycarbonyl nitrogen protecting group may be introduced, for example, by reaction of an unprotected compound with di-tert-butyl dicarbonate, conveniently in the presence of a base such as 4-dimethylaminopyridine. Suitable solvents include halogenated hydrocarbons, such as dichloromethane.

The compounds of formula VII may be prepared by a method analogous to that used to prepare the compounds of formula V.

The compounds of formula XIII and XIV are known or may be prepared by conventional methods, for example by reducing a corresponding amide or nitrile using borane.

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 $\mu$l of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 $\mu$M Fluo3-AM dye (obtained from Molecular Probes Inc., Eugene, Oreg.) in buffer in each well. After the incubation, each well is washed once with 100 $\mu$l buffer, 200 $\mu$l of buffer is added and the plates are incubated for 30 minutes.

Solutions for use in the test are also prepared as follows. 30 $\mu$M, 10 $\mu$M, 3 $\mu$M and 1 $\mu$M dilutions of test compound are prepared using buffer from a 10 mM solution of test compound in DMSO. 100 $\mu$M cyclothiazide solution is prepared by adding 3 $\mu$l of 100 mM cyclothiazide to 3 ml of buffer. Control buffer solution is prepared by adding 1.5 $\mu$l DMSO to 498.5 $\mu$l of buffer.

Each test is then performed as follows. 200 $\mu$l of control buffer in each well is discarded and replaced with 45 $\mu$l of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 $\mu$l of buffer and 45 $\mu$l of test compound in buffer in appropriate wells. A second fluorescent reading is taken after 5 minutes incubation. 15 $\mu$l of 400 $\mu$M glutamate solution is then added to each well (final glutamate concentration 100 4 $\mu$M), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 $\mu$M cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM): 140 NaCl, 5 KCl, 10 HEPES, 1 MgCl$_2$, 2 CaCl$_2$, 10 glucose, pH=7.4 with NaOH, 295 mOsm kg$^{-1}$. The intracellular recording solution contains (in nM): 140 CsCl, 1 MgCl$_2$, 10 HEPES, (N-[2-hydroxyethyl]piperazine-N$^1$-[2-ethanesulfonic acid]) 10 EGTA (ethylene-bis (oxyethylenenitrilo) tetraacetic acid), pH=7.2 with CsOH, 295 mOsm kg$^{-1}$. With these solutions, recording pipettes have a resistance of 2–3 M$\Omega$. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 $\mu$M, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an EC$_{50}$ value, indicative of the potency of the test compound. Reversibility of test compound activity is determined by assessing control glutamate 1 mM responses. Once the control responses to the glutamate challenge are re-established, the potentiation of these responses by 100 $\mu$M cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
Tablets each containing 60 mg of active ingredient are made as follows:

| | |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following preparations and Examples illustrate the invention.

PREPARATION 1

2-(4-Benzyloxyphenyl)propionitrile

To a −15° C. solution of 4-benzyloxyacetophenone (500 mg, 2.2 mmol)and tosylmethyl isocyanide (650 mg, 3.3 mmol) in 10 mL of dry dimethoxyethane was added 2 mL of a warm solution of potassium tert-butoxide (500 mg, 4.5 mmol) in tert-butyl alcohol dropwise at a rate to maintain the temperature below 0° C. The reaction was stirred at −5° C. for 45 min after addition was complete. The cooling bath was removed and the reaction stirred for 2.5 h more. The mixture was concentrated in vacuo to a volume of 2 mL and diluted with 10 mL of water. The organic was extracted four times with ethyl acetate, and the combined organic portions were dried ($MgSO_4$), filtered and concentrated in vacuo. The crude product was purified by flash chromatography ($SiO_2$, EtOAc/Hexanes; 0–25%, gradient) to yield 370 mg (71%) of the pure product. Electrospray Mass Spectrum: 237.1.

Analysis calculated for $C_{16}H_{15}NO$: Calculated: C; 81.00, H; 6.30, N; 5.90. Found: C; 81.04, H; 6.64, N; 6.17.

PREPARATION 2

2-(4-Benzyloxyphenyl)propylamine hydrochloride

To an ambient solution of the product of Preparation 1 (1.6 g, 6.75 mmol) in 10 ml of the tetrahydrofuran was added borane dimethylsulfide (0.75 ml of the 10 M solution, 7.5 mmol). The reaction mixture was refluxed for 1 h. The mixture was cooled to ambient temperature and the solvent was removed in vacuum. The crude product was dissolved in ether and this mixture was treated with a saturated solution of HCl in methanol (3×20 mL). The resulting white product was precipitated out of ether and collected by filtration to give 1.6 g (86%) of the pure product. Electospray Mass Spectrum: 242 (M-HCl). Analysis calculated for $C_{16}H_{20}ClNO$: % C, 69.30; % H, 7.20; % N, 5.10. Found: % C, 68.60; % H, 7.19; % N, 4.80.

PREPARATION 3

N-2-(4-Benzyloxyphenyl)propyl 2-propanesulfonamide

A 0° C. suspension of the material from Preparation 2 (10.8 g, 39 mmol) in dichloromethane (200 ml) was treated with 1,8-diazabicyclo[5.4.0]undec-ene (14.4 mL, 116 mmol) followed by 2-propylsulfonyl chloride (4.8 mL, 43 mmol). The reaction mixture was stirred at 0° C. for 1 h and at ambient temperature for an extra 2 h. The reaction was stopped by the addition of water (100 ml). The organic material was extracted with dichloromethane (3×200 ml). The combined organic fraction was then washed with water (3×200 ml), brine (100 ml), dried over potassium carbonate, and concentrated in vacuo to give the crude material which was further purified by flash chromatography ($SiO_2$, 20% EtOAc: Hexane) to give 7.3 g (54%) of the pure product. NMR was consistent with the proposed title structure. Electrospray Mass Spectrum :$M^+$=346. Analysis calculated for $C_{19}H_{25}NO_3S$: % C, 65.68; % H, 7.25; % N, 4.03. Found: % C, 65.63; % H, 7.31; % N, 4.07.

PREPARATION 4

N-t-butoxycarbonyl-N-(2-(4-hydroxyphenyl)propyl) 2-propanesulfonamide

The product of Preparation 3 (7.6 g, 23.8 mmol) was dissolved in dichloromethane (100 ml) and to this mixture as added di-text-butyl dicarbonate (5.71 g, 26.2 mmol) and 4-dimethylaminopyridine ( 1.45 g, 11.9 mmol). The reaction was stirred at ambient temperature for 1 hour. The reaction was washed with a saturated aqueous solution of sodium hydrogen sulfate and brine. The organic fraction was dried over magnesium sulfate and concentrated under vacuo. The protected sulfonamide (9.00 g, 21.0 mmol) was dissolved in ethyl acetate: $H_2O$ (5:1) and ammonium formate (2.0 g, 31.5 mmol) added to the mixture. Then palladium on carbon (10%) (0.9 g) was added to the reaction and this was stirred at ambient temperature for 6 hours. The suspension was filtered through celite and the resulting solution concentrated in vacuo to give 5.51 g (78%) of title product. Field Desorption Mass Spectrum: M=329.1. Analysis calculated for $C_{15}H_{23}NO_5S$: % C, 54.69; % H, 7.04; % N, 4.25. Found: % C, 53.70; % H, 7.72; % N, 4.04.

PREPARATION 5

2-(4-Bromophenyl)propylamine hydrochloride

To a −15° C. solution of 50.0 g (251.2 mmol) of 4-bromoacetophenone and 49.0 g ( 251.2 mmol) of tosylmethyl iso-cyanide in 800 mL of dry dimethoxyethane was added a hot solution of 50.7 g ( 452.2 mmol) of potassium tert-butoxide in 230 mL of tert-butyl alcohol dropwise at a rate to maintain the temperature below 0° C. The reaction was stirred at −5° C. for 45 min after addition was complete. The cooling bath was removed and the reaction stirred for 2.5 h more. The mixture was concentrated in vacuo to a volume of 200 mL and diluted with 500 mL of water. The aqueous mixture was extracted four times with diethyl ether, and the combined organic portions were dried ($MgSO_4$), filtered and concentrated in vacuo. The residue was dissolved in 55 mL of tetrahydrofuran and heated to reflux. To the refluxing solution was added slowly dropwise 27.6 mL ( 276.3 mmol) of 10.0 M borane-dimethylsulfide complex. Refluxing was continued for 20 min after addition was complete. The mixture was cooled to ambient temperature and methanol saturated with hydrogen chloride was added very slowly until pH 2 was achieved. The mixture was concentrated in vacuo and the residue was dissolved in methanol and concentrated in vacuo again. The solid residue was suspended in 125 mL of ethanol, filtered, rinsed with ethanol then diethyl ether. The white solid was dried in vacuo to afford 25.4 g (40%) of the title compound. The filtrate was concentrated in vacuo and suspended in diethyl ether. The solid was filtered, rinsed with diethyl ether and dried in vacuo to afford another 15.6 g (25%) of the title compound.

PREPARATION 6

N-2-(4-bromophenyl)propyl 2-propanesulfonamide

A solution of 15.0 g (59.9 mmol) of the material from Preparation 5 and 18.4 mL (131.8 mmol) of triethylamine in 150 mL of dichloromethane was stirred 20 min at room temperature, then cooled to 0° C. and treated dropwise over 5 min with 8.1 mL (71.9 mmol) of 2-propylsulfonyl chloride in 10 mL of dichloromethane. After stirring overnight at room temperature, the reaction was washed once with 200 mL of 10% aqueous sodium bisulfate, the layers separated and the aqueous layer extracted twice with 100 mL each of dichloromethane. The combined organic extracts were dried ($MgSO_4$), filtered and concentrated in vacuo. Chromatography (500 g of silica gel, 30% ethyl acetate/hexane) of the residue afforded 11.0 g (57%) of the title compound.

PREPARATION 7

3-Tributyltin-2-cyclopenten-1-one

A −20° C. solution of hexabutylditin (4.6 g, 7.9 mmol) in dry THF (15 ml) was treated with nBuLi (4.9 ml, 7.9 mmol, 1.6 M solution in hexanes). The reaction mixture was stirred at −20° C. for 30 mins and then cooled to −78° C. The mixture was treated with 3-ethoxy-2-cyclopenten-1-one (1.0 g, 7.9 mmol) and the reaction mixture stirred at −78° C. for 30 mins. A saturated, aqueous solution of ammonium chloride (2 ml) followed by water (30 ml) and the organic extracted with hexanes (2×30 ml). The combined organic layers were washed with brine (20 ml), dried over magnesium sulfate and concentrated in vacuo. This gave 2.7 g (93%) of the crude title compound which was used without further purification. NMR was consistent with the title structure.

PREPARATION 8

N-2-(4-(1-(3-oxo)cyclopentenyl)phenyl)propyl 2-propanesulfonamide

A solution of the product of Preparation 6 (1.0 g, 3.22 mmol) in dry, degassed THF (15 ml) was treated with the product of Preparation 7 (1.8 g, 4.83 mmol), and dichlorobis (triphenylphosphine)palladium(II) (45 mg, 0.06 mmol). The reaction mixture was heated to reflux for 48 hrs. The mixture was cooled and partitioned between acetonitrile and hexanes. The acetonitrile layer was washed with hexanes (3×20 ml), then concentrated in vacuo. The crude product was further purified by flash chromatography ($SiO_2$, 70% EtOAc:hexanes) to give 0.71 g (68%) of title compound as a pure product. NMR was consistent with proposed title structure. Field Desorption Mass Spectrum: M=321.1. Analysis calculated for $C_{18}H_{28}N_2O_3S$: % C, 61.33; % H, 8.01; % N, 7.95. Found: % C, 61.08; % H, 7.78; % N, 8.07

PREPARATION 9

N-2-(4-(3-oxocyclopentyl)phenyl)propyl 2-propanesulfonamide

A solution of the material from Preparation 8 (0.15 g, 0.47 mmol) in EtOAc (5 ml) was treated with palladium on carbon (0.02 g, 10 mole %) under a hydrogen atmosphere. The mixture was stirred at ambient for 4 hrs and then heated to 50° C. for 2 hrs. The reaction was filtered through a celite cake and the filtrate concentrated in vacuo. The crude mixture of both title products was purified by flash chromatography ($SiO_2$, 70% EtOAc:hexanes) to give the title compound (0.06 g) and N-2-(4-(3-hydroxycyclopentyl) phenyl)-propyl 2-propanesulfonamide (0.05 g). NMR was consistent with the proposed title structure. Field Desorption Mass Spectrum: M=323. Analysis calculated for $C_{17}H_{25}NO_3S$: % C, 63.13; % H, 7.91; % N, 4.33. Found: % C, 63.34; % H, 7.76; % N, 4.30.

EXAMPLE 1

N-2-[4-(3-(3-piperidinyl)propyloxy)phenyl]propyl 2-propanesulfonamide

The product of Preparation 4 (325 mg, 0.91 mmol) was dissolved in dimethylformamide (3 mL)and sodium hydride (44 mg, 1.1 mmol) was added. After 15 minutes, 3-(3-N-t-butyloxycarbonylpiperidinyl)propyl bromide (321 mg, 1.1 mmol) and potassium iodide (45 mg, 0.027 mmol) were added to the reaction and the mixture was stirred at 65° C. for 2 hours. The reaction mixture was partitioned between dichloromethane and water. The organic was washed with brine, dried over sodium sulfate and concentrated in vacuo. Chromatography ($SiO_2$, 5% methanol/dichloromethane) gave 479 mg of the pure product which was dissolved in 3 mL of the dichloromethane: TFA (1:1). The mixture was stirred at ambient temperature for 45 minutes. The reaction mixture was then partitioned between dichloromethane and water. The organic phase was dried over sodium sulfate and concentrated in vacuo to give 275 mg (79%) of the title compound. Electrospray Mass Spectrum: M=383.5. Analysis calculated for $C_{20}H_{34}N_2O_3S.0.5H_2O$: % C, 61.35; % H, 9.00; % N, 7.15. Found: % C, 61.40; % H, 8.24; % N, 6.88.

EXAMPLE 2

N-2-[4-(2-(3-piperidinyl)ethoxy)phenyl]propyl 2-propanesulfonamide

The title compound was prepared from the product of Preparation 4 and 2-(3-piperidinyl)ethyl bromide as described in Example 1. Electrospray Mass Spectrum: M=369.1. Analysis calculated for $C_{19}H_{32}N_2O_3S.0.5H_2O$: % C, 60.44; % H, 8.81; % N, 7.42. Found: % C, 60.78; % H, 8.46; % N, 7.43.

EXAMPLE 3

N-2-[4-(3-(4-piperidinyl)propoxy)phenyl]propyl 2-propanesulfonamide

The title compound was prepared from the product of Preparation 4 and 3-(4-piperidinyl)propyl bromide as described in Example 1. Electrospray Mass Spectrum: M 383.5. Analysis calculated for $C_{20}H_{34}N_2O_3S$: % C, 62.78; % H, 8.96; % N, 7.32. Found: % C, 62.91; % H, 8.81; % N, 7.21.

EXAMPLE 4

Mixture of N-2-[4-(6-keto-3-piperidinyl)phenyl] propyl 2-propanesulfonamide and N-2-[4-(2-keto-4-piperidinyl)phenyl]propyl 2-propanesulfonamide The product of Preparation 9 (1.0 g, 3.1 mMol), hydroxylamine hydrochloride (362 mg, 5.5 mmol), and sodium acetate (466 mg, 3.4 mMol) were placed in methanol (15 mL) and stirred at ambient temperature under nitrogen for 45 minutes. The solution was then concentrated under reduced pressure to yield a white solid. This material was taken into methylene chloride (100 mL) and washed once with water, dried over $K_2CO_3$, and concentrated under reduced pressure to yield 1.04 g. of a white solid. The material along with sodium hydroxide (643 mg) was placed in dioxane/water 3:4 (50 mL) and p-toluenesulfonyl chloride (1.33 g) was added portion wise while stirring at 0° C. under nitrogen. The reaction mixture was then allowed to warm to ambient temperature and stirred overnight. In the morning, the dioxane was evaporated off and the resulting water layer was extracted two times with methylene chloride (50 mL). The combined organic extractions were washed once with water, dried over $K_2CO_3$, and concentrated under reduced vacuum to yield a tan solid (900 mg). Purification was achieved by Chromatotron (Model 8924, available from Harrison Research, 840 Moana Court, Palo Alto, Calif. 94306, USA) silica gel chromatography using a 4000 micron rotor and eluting with a solvent of ethyl acetate/methanol 9:1 to yield the title mixture of compounds (560 mg) as a yellow oil. The mixture could not be separated. NMR was consistent with the proposed mixture. IR stretch was at 1659.67 $^{cm-1}$ for the amide carbonyl. Ion spray mass spectrum: M+1=339.2.

EXAMPLES 5 AND 6

N-2-[4-(3-piperidinyl)phenyl]propyl 2-propanesulfonamide and N-2-[4-(4-piperidinyl) phenyl]propyl 2-propanesulfonamide The product of Example 4 (350 mg., 1.0 mMol) was placed in tetrahydrofuran (10 mL) and borane-tetrahydrofuran complex (12 mL of 1.0 M, 12.0 mMol) was added syringe wise while stirring at ambient temperature under nitrogen. The reaction was then stirred for 16 hours at ambient temperature. A 1:1 methanol/tetrahydrofuran solution (1mL) was added dropwise followed by 5.0 N sodium hydroxide solution (5 mL) dropwise. The reaction was then refluxed for 5 hours, cooled to ambient temperature and the organic layer was separated and concentrated under reduced vacuum. The resulting oil was taken into methylene chloride (50 mL). washed once with water (50 mL) , dried over $K_2CO_3$ and concentrated under reduced vacuum to yield 438 mg. of a viscous oil containing a mixture of both amines. Separation and purification was achieved by Chromatotron silica gel chromatography using a 4000 micron rotor and eluting with an isocratic solvent of methylene chloride/methanol 9:1 and 1% ammonium hydroxide. The faster eluting material contained N-2-[4-(3-piperidinyl)phenyl] propyl 2-propanesulfonamide (90 mg) as a white foam. NMR was consistent with the proposed structure. Ion spray mass spectrum: M+1 325.4 Analysis for $C_{17}H_{28}N_2O_2S$: Theory: % C, 62.93; % H, 8.70; % N, 8.63.

Found: % C, 62.89; % H, 8.55; % N, 8.55.

The slower eluting material contained N-2-[4-(4-piperidinyl)phenyl]propyl 2-propanesulfonamide (77 mg) as a white foam. NMR was consistent with the proposed structure. Ion spray mass spectrum: M+1 325.4 Analysis for $C_{17}H_{28}N_2O_2S$: Theory: % C, 62.93; % H, 8.70; % N, 8.63. Found: % C, 62.09; % H, 8.48; % N, 8.39.

EXAMPLE 7

N-2-[4-(N-methyl-3-piperidinyl) phenyl]propyl 2-propanesulfonamide

The product from Example 5 (60 mg, 0.19 mMol) was subjected to 96% formic acid (0.75 mL) and 37% formaldehyde (0.75 mL) and heated at 80° C. for one hour with stirring. The reaction mixture was then cooled to ambient temperature and the acidic media was made basic (pH 12) using 50% sodium hydroxide and ice. The resulting percipitate was extracted with methylene chloride (50 mL), washed once with water (50 mL), dried over $K_2CO_3$, and concentrated under reduced vacuum to yield a viscous oil (67.3 mg). Purification was achieved by Chromatotron silica gel chromatography using a 1000 micron rotor and eluting with an isocratic solvent of methylene chloride/methanol 9:1 and 1% ammonium hydroxide to yield the title compound (37.8 mg) as a white foam. (Yield=59%). NMR was consistent with the proposed structure. Ion spray mass spectrum: M+1 339.2.

EXAMPLE 8

N-2-[4-(N-methyl-4-piperidinyl)phenyl]propyl 2-propanesulfonamide

The product of Example 6 (50 mg, 0.15 mmol) was subjected to 96% formic acid (0.6 mL) and 37% formaldehyde (0.6 mL) as described in Example 7 to yield an oil (53.4 mg). Purification was achieved by Chromatotron silica gel chromatography using a 1000 micron rotor and eluting with an isocratic solvent of methylene chloride/methanol 9:1 and 1% ammonium hydroxide to yield the title compound (20.3 mg) as a viscous oil. NMR was consistent with the proposed structure. Ion spray mass spectrum: M+1=339.2. Analysis calculated for $C_{18}H_{30}N_2O_2S$-½ $H_2O$: % C, 62.17; % H, 8.99; % N, 8.06. Found: % C, 62.24; % H, 8.79; % N, 7.95.

We claim:
1. A compound of the formula:

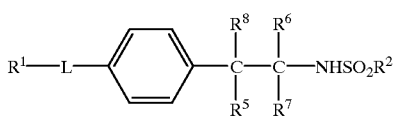

wherein:

$R^1$ represents a carbon-linked 4 to 7 membered saturated heterocyclic ring containing as the hetero ring members a group $NR^a$ and a group $X^a$ in which $X^a$ represents $CH_2$, CO, O, S or $NR^b$; $R^a$ represents hydrogen or (1–4C)alkyl; and $R^b$ represents hydrogen or (1–4C)alkyl;

L represents a bond or a group of formula —$(L^a)_m$—X—$(L^b)_n$— in which X represents O, S, $NR^c$, CONH or NHCO; $L^a$ represents (1–4C)alkylene; $L^b$ represents (1–4C)alkylene; m is zero or 1; n is zero or 1; and $R^c$ is hydrogen or (1–4C)alkyl;

$R^2$ represents (1–6C)alkyl, (3–6C)cycloalkyl, (1–6C)fluoroalkyl, (1–6C)chloroalkyl, (2–6C)alkenyl, (1–4C)alkoxy(1–4C)alkyl, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; and either (a) one or two of $R^5$, $R^6$, $R^7$ and $R^8$ represents hydrogen; (1–6C)alkyl; aryl(1–6C)alkyl; (2–6C)alkenyl; aryl (2–6C)alkenyl or aryl, or (b) two of $R^5$, $R^6$, $R^7$ and $R^8$ together with the carbon atom or carbon atoms to which they are attached form a (3–8C) carbocyclic ring; and the remainder of $R^5$, $R^6$, $R^7$ and $R^8$ represent hydrogen; or a pharmaceutically acceptable salt thereof, provided that when L represents a group of formula —$(L^a)_m$—X—$(L^b)_n$— and m is 0, $R^1$ is not pyrrolidinyl.

2. A compound as claimed in claim 1, wherein $R^1$ represents an azetidinyl, pyrrolidinyl, piperidinyl, morpholinyl, thiomorpholinyl, piperazinyl, hexahydropyrimidyl, tetrahydro-1,3-oxazinyl, tetrahydro-1,3-thiazinyl or hexahydroazepinyl group.

3. A compound as claimed in claim 2, wherein $R^1$ represents a group selected from (a)

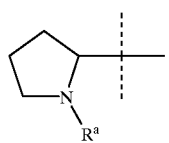

(b)

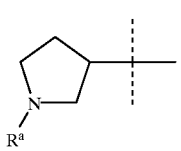

(c)

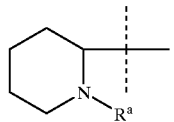

(d)

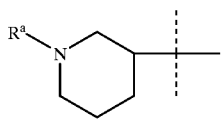

(e)

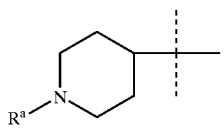

(f)

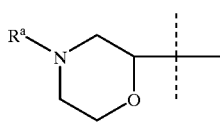

(g)

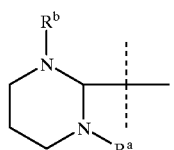

(h)

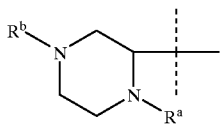

(i)

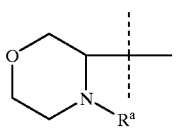

(j)

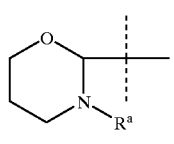

(k)

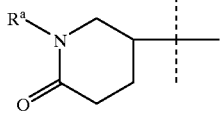

(l)

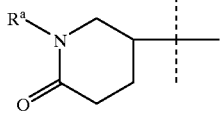

wherein $R^a$ represents hydrogen or (1–4C)alkyl; and $R^b$ represents hydrogen or (1–4C)alkyl.

4. A compound as claimed in claim 3, wherein $R^1$ is 3-piperidinyl, 4-piperidinyl, 6-oxo-3-piperidinyl, 2-oxo-4-piperidinyl, N-methyl-3-piperidinyl or N-methyl-4-piperidinyl.

5. A compound according to claim 4, wherein $R^2$ represents (1–6C)alkyl, (1–6C)fluoroalkyl, (2–6C)alkenyl, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group.

6. A compound as claimed in claim 5, wherein $R^2$ represents methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino.

7. A compound as claimed in claim 6, wherein $R^2$ represents ethyl, 2-propyl or dimethylamino.

8. A compound according to claim 7 wherein $R^6$ and $R^7$ each represents hydrogen.

9. A compound as claimed in claim 8, in which $R^8$ represents methyl and $R^5$ represents hydrogen.

10. A compound according to claim 9, in which L represents a bond or a group of formula $L^aX$.

11. A compound as claimed in claim 10, in which $L^a$ is methylene, ethylene, propylene and butylene, and X is O.

12. A pharmaceutical composition, which comprises a compound as claimed in claim 1 and a pharmaceutically acceptable diluent or carrier.

13. A method of potentiating glutamate receptor function in a mammal requiring such treatment, which comprises administering an effective amount of a compound as claimed in claim 1.

14. A method of treating a cognitive disorder; a neurodegenerative disorder; age-related dementia; age-induced memory impairment; a movement disorder; reversal of a drug-induced state; depression; attention deficit disorder; attention deficit hyperactivity disorder; psychosis; cognitive deficit associated with psychosis; or drug-induced psychosis in a patient, which comprises administering to a patient in need thereof an effective amount of a compound as claimed in claim 1.

15. A method for improving memory or learning ability in a patient, which comprises administering to a patient in need thereof an effective amount of a compound as claimed in claim 1.

* * * * *